US009317655B2

(12) United States Patent
Lu et al.

(10) Patent No.: US 9,317,655 B2
(45) Date of Patent: Apr. 19, 2016

(54) SYSTEMS AND METHODS FOR DETECTING THE PRESENCE OF A BIOLOGICAL STATUS USING PLOT

(75) Inventors: Jiuliu Lu, Homestead, FL (US); Zihua Wang, Newton, MA (US); Antonio Arevalo Reyes, Middleton, MA (US); Erik Alan Gustafson, Norwood, MA (US); John Steven Riley, Miami, FL (US)

(73) Assignee: Beckman Coulter, Inc., Brea, CA (US)

( * ) Notice: Subject to any disclaimer, the term of this patent is extended or adjusted under 35 U.S.C. 154(b) by 907 days.

(21) Appl. No.: 13/509,347

(22) PCT Filed: Nov. 11, 2010

(86) PCT No.: PCT/US2010/056387
§ 371 (c)(1),
(2), (4) Date: Jul. 23, 2012

(87) PCT Pub. No.: WO2011/060174
PCT Pub. Date: May 19, 2011

(65) Prior Publication Data
US 2012/0283957 A1    Nov. 8, 2012

Related U.S. Application Data

(60) Provisional application No. 61/261,109, filed on Nov. 13, 2009.

(51) Int. Cl.
*G01N 33/48*    (2006.01)
*G01N 33/50*    (2006.01)
(Continued)

(52) U.S. Cl.
CPC ............... *G06F 19/26* (2013.01); *G06F 19/12* (2013.01); *G06F 19/18* (2013.01); *G06T 11/206* (2013.01); *G06F 19/24* (2013.01)

(58) Field of Classification Search
None
See application file for complete search history.

(56) References Cited

U.S. PATENT DOCUMENTS 5,210,015 A    5/1993    Gelfand et al.
5,487,972 A    1/1996    Gelfand et al.
(Continued)

FOREIGN PATENT DOCUMENTS

CN    10108872 A    8/2007
EP    1 529 847 B1    5/2005
(Continued)

OTHER PUBLICATIONS

Chinese Office Action mailed on Aug. 6, 2014 for CN Patent Application No. 201080051501.2, with English Translation, 25 pages.
(Continued)

*Primary Examiner* — Russell S Negin
(74) *Attorney, Agent, or Firm* — Kilpatrick Townsend & Stockton LLP

(57) ABSTRACT

Systems and methods for identifying Methicillin resistant strains of *Staphylococcus aureus* (MRSA) in a sample are used that are based on the fact that an MRSA positive sample should have roughly the same copy numbers of mecA, SCCmec, and a *Staphylococcus aureus*-specific target gene sequence. The systems and methods may further present the three assays simultaneously on a 2-D plot with each axis of the plot 120 degrees apart. According to one embodiment, a Y plot is used for the 2-D display. If a given sample has similar readings of mecA, SCCmec, and a *Staphylococcus aureus*-specific target gene sequence, the sample's measured copy numbers of mecA, SCCmec, and the *Staphylococcus aureus*-specific target gene sequence can plot close to the origin regardless of the sample's absolute assay readings. With the help of this transformation, a boundary function can be defined that can be used to distinguish MRSA-positive samples from MRSA-negative samples.

33 Claims, 6 Drawing Sheets

(51) Int. Cl.
  G06F 19/26 (2011.01)
  G06F 19/12 (2011.01)
  G06F 19/18 (2011.01)
  G06T 11/20 (2006.01)
  G06F 19/24 (2011.01)

(56) References Cited

U.S. PATENT DOCUMENTS

| | | | |
|---|---|---|---|
| 5,702,895 | A | 12/1997 | Matsunaga et al. |
| 5,804,375 | A | 9/1998 | Gelfand et al. |
| 6,156,507 | A | 12/2000 | Hiramatsu et al. |
| 7,527,929 | B2 | 5/2009 | McKernan et al. |
| 7,659,895 | B2 | 2/2010 | Kandogan |
| 2003/0030637 | A1 | 2/2003 | Grinstein et al. |
| 2004/0241824 | A1 | 12/2004 | Schrenzel et al. |
| 2010/0110103 | A1* | 5/2010 | Ramirez et al. ............ 345/619 |

FOREIGN PATENT DOCUMENTS

| | | |
|---|---|---|
| EP | 1 370 694 B1 | 1/2007 |
| JP | 2004-531251 A | 10/2004 |
| WO | 02/082086 A2 | 10/2002 |
| WO | WO 2008-129428 A2 | 10/2008 |
| WO | WO 2009/018000 A1 | 2/2009 |

OTHER PUBLICATIONS

Becker, K., et al., "Does Nasal Cocolonization by Methicillin-Resistant Coagulase-Negative Staphylococci and Methicillin-Susceptible *Staphylococcus aureus* Strains Occur Frequently Enough to Represent a Risk of False-Positive Methicillin-Resistant *S. aureus* Determinations by Molecular Methods?" *Journal of Clinical Microbiology*, Jan. 2006, pp. 229-231, vol. 44, No. 1, Copyright 2006, American Society for Microbiology.

Bustin, S. A., et al., "Quantitative real-time RT-PCR—a perspective," *Journal of Molecular Endocrinology*, 2005, pp. 597-601, vol. 34, Copyright 2005, Society for Endocrinology.

Cuny, C., et al., "PCR for the identification of methicillin-resistant *Staphylococcus aureus* (MRSA) strains using a single primer pair specific for SCC*mec* elements and the neighbouring chromosome-borne *orfX*," *Clinical Microbiology and Infection*, Oct. 2005, pp. 834-837, vol. 11, No. 10, Copyright 2005 by the European Society of Clinical Microbiology and Infectious Diseases.

Farley, J. E., et al., "Comparison of the BD GeneOhm Methicillin-Resistant *Staphylococcus aureus* (MRSA) PCR Assay to Culture by Use of BBL CHROMagar MRSA for Detection of MRSA in Nasal Surveillance Cultures from an At-Risk Community Population," *Journal of Clinical Microbiology*, Feb. 2008, pp. 743-746, vol. 46, No. 2, Copyright 2008, American Society for Microbiology.

Francois, P., et al., "Rapid Detection of Methicillin-Resistant *Staphylococcus aureus* Directly from Sterile or Nonsterile Clinical Samples by a New Molecular Assay," *Journal of Clinical Microbiology*, Jan. 2003, pp. 254-260, vol. 41, No. 1, Copyright 2003, American Society for Microbiology.

Heid, C. A., et al., "Real Time Quantitative PCR," *Genome Research*, 1996, pp. 986-994, vol. 6, Copyright Cold Spring Harbor Laboratory Press, Downloaded from genome.cship.org on Jan. 14, 2011, Published by Cold Spring Harbor Laboratory Press.

Heusser, R., et al., "Mosaic Staphylococcal Cassette Chromosome *mec* Containing Two Recombinase Loci and a New *mec* Complex, B2," *Antimicrobial Agents and Chemotherapy*, Jan. 2007, pp. 390-393, vol. 51, No. 1, Copyright 2007, American Society for Microbiology.

Huletsky, A., et al., "New Real-Time PCR Assay for Rapid Detection of Methicillin-Resistant *Staphylococcus aureus* Directly from Specimens Containing a Mixture of Staphylococci," *Journal of Clincal Microbiology*, May 2004, pp. 1875-1884, vol. 42, No. 5, Copyright 2004, American Society for Microbiology.

Ito, T., et al., "Structural Comparison of Three Types of Staphylococcal Cassette Chromosome *mec* Integrated in the Chromosome in Methicillin-Resistant *Staphylococcus aureus*," *Antimicrobial Agents and Chemotherapy*, May 2001, pp. 1323-1336, vol. 5, No. 5, Copyright 2001, American Society for Microbiology.

Ito, T., et al., "Novel Type V Staphylococcal Cassette Chromosome *mec* Driven by a Novel Cassette Chromosome Recombinase, *ccrC*," *Antimicrobial Agents and Chemotherapy*, Jul. 2004, pp. 2637-2651, vol. 48, No. 7, Copyright 2004, American Society for Microbiology.

Mullis, K.B., et al., "Specific Synthesis of DNA in Vitro Via a Polymerase-Catalyzed Chain Reaction," *Methods Enzymol*, Polymerase Chain Reaction, pp. 335-350, vol. 155, 1987.

Noto, M. J., et al., "Gene Acquisition at the Insertion Site for SCC*mec*, the Genomic Island Conferring Methicillin Resistance in *Staphylococcus aureus*," *Journal of Bacteriology*, Feb. 2008, pp. 1276-1283, vol. 190, No. 4, Copyright 2008, American Society for Microbiology.

Sinsimer, D., et al., "Use of a Multiplex Molecular Beacon Platform for Rapid Detection of Methicillin and Vancomycin Resistance in *Staphylococcus aureus*," *Journal of Clinical Microbiology*, Sep. 2005, pp. 4585-4591, vol. 43, No. 9, Copyright 2005, American Society for Microbiology.

Japanese Office Action mailed on Dec. 11, 2014 for JP Patent Application No. 2012-538984, with English Translation, 10 pages.

The International Search Report of the International Searching Authority for Application No. PCT/US2010/056387, mailed on Apr. 4, 2011, 5 pages.

The Written Opinion of the International Searching Authority for Application No. PCT/US2010/056387, mailed on Apr. 4, 2011, 10 pages.

Machado, F., et al., "Visual RBF Network Design Based on Star Coordinates," *Advances in Engineering Software*, vol. 40, No. 9, Sep. 1, 2009, pp. 913-919, Elsevier Science, Oxford, GB.

Kolbert, C.P. et al. "Branched-DNA Assay for Detection of the *mecA* Gene in Oxacillin-Resistant and Oxacillin-Sensitive Staphylococci," *Journal of Clinical Microbiology*, Sep. 1998, pp. 2640-2644, vol. 36, No. 9.

Strandén, A. et al. Molecular Typing of Methicillin-Resistant *Staphylococcus auereus*: Can PCR Replace Pulsed-Field Gel Electrophoresis? *Journal of Clinical Microbiology*, Jul. 2003, pp. 3181-3186, vol. 41, No. 7.

Zhang, K. et al. "New Quadriplex PCR Assay for Detection of Methicillin and Mupirocin Resistance and Simultaneous Discrimination of *Staphylococcus auereus* form Coagulase-Negative Staphylococci," *Journal of Clinical Microbiology*, Nov. 2004, pp. 4947-4955, vol. 42, No. 11.

Japanese Office Action mailed on Sep. 11, 2015 for JP Patent Application No. 2012-538984, with English Translation, 7 pages.

* cited by examiner

SYSTEMS AND METHODS FOR DETECTING THE PRESENCE OF A BIOLOGICAL STATUS USING PLOT

CROSS-REFERENCE TO RELATED APPLICATION

This application is a National Stage of International Application No. PCT/US2010/056387, filed Nov. 11, 2010, which claims the benefit of priority to U.S. Provisional Application No. 61/261,109, filed Nov. 13, 2009, the disclosures of which are herein incorporated by reference.

REFERENCE TO A "SEQUENCE LISTING," A TABLE, OR A COMPUTER PROGRAM LISTING APPENDIX SUBMITTED AS AN ASCII TEXT FILE

The Sequence Listing written in file -103-1.TXT, created on Jun. 19, 2012, 8,192 bytes, machine format IBM-PC, MS-Windows operating system, is hereby incorporated by reference in its entirety for all purposes.

BACKGROUND

Methicillin resistant strains of *Staphylococcus aureus* (MRSA) are implicated in infections with serious outcomes including nosocomial outbreaks, and show resistance to a wide range of antibiotics, thus limiting the treatment options. Healthcare associated MRSA is of particular clinical importance because it is not only predictably cross resistant to all penicillins and cephalosporins, but is also typically resistant to multiple other commonly used antibiotics. Treatment of MRSA infections generally require more expensive and often more toxic antibiotics, which are normally used as the last line of defense. Therefore, rapid detection of MRSA is clinically crucial for both treatment and infection control measures.

Detection of MRSA is further complicated by the fact that MRSA can often co-colonize with multiple other related bacteria, including methicillin-sensitive *Staphylococcus aureus* (MSSA), methicillin-resistant coagulase-negative staphylococci (MR-CoNS) and/or methicillin-sensitive coagulase-negative staphylococci (MS-CoNS).

Traditional methods for the detection of MRSA in clinical microbiology laboratories involve culturing the bacteria from a sample as the first step for the isolation and differentiation of MRSA from MSSA and MR-CoNS. This approach is time-consuming and requires a minimum of 20 to 24 hours until a result is known.

A number of molecular based methods have been published for the detection of methicillin resistant *Staphylococcus aureus* (MRSA) and differentiating it from methicillin sensitive *Staphylococcus aureus* (MSSA). One such method targets two separate regions of MRSA, the mecA gene of the *Staphylococcus* cassette chromosome (SCCmec, responsible for methicillin resistance) and spa gene of *Staphylococcus aureus* (U.S. Pat. No. 5,702,895, Sinsimer, et al., Journal of Clinical Microbiology, September 2005, 4585-4591). Unambiguous detection of MRSA using this approach is hampered by the co-existence of non-*Staphylococcus aureus* strains such as methicillin resistant coagulase negative Staphylococci (MR-CoNS) which also harbors the mecA gene for methicillin resistance (Becker, et. al. Journal of Clinical Microbiology, January 2006, p 229-231).

A more recent molecular approach utilizes primers and probes to SCCmec and the flanking region of the *Staphylococcus aureus* genome (U.S. Pat. No. 6,156,507, Huletsky, et. al. Journal of Clinical Microbiology, May 2004, p 1875-1884). SCCmec is a mobile genetic element that carries the mecA gene and inserts at a specific site, attBscc, at the 3'-end of the orfX gene. The left extremity of SCCmec is contiguous with the non-orfX side of attBscc while the right extremity of SCCmec is contiguous with the orfX side of attBscc (Ito, et al., Antimicrob. Agent Chemother. 2001, 45, p 1323-1336; Ito et al., Antimicrob. Agent Chemother. 2004, 48, p 2637-2651, Noto, et al., J. Bacteriol. 2008, 190:1276-1283). This approach infers the presence of the mecA gene from the detection of the SCCmec/orfX junction. This approach requires the use of multiple primers as there have been several different types of SCCmec described. This approach is also subject to false positive results due to the presence of SCCmec cassettes that do not contain the mecA gene (Farley, et. al. Journal of Clinical Microbiology, February 2008, p 743-746) and false negative results due to newly emerged SCCmec types not covered by the assay (Heusser, et al., Antimicrob. Agents Chemother. January 2007, p 390-393).

Another approach utilizes one primer in a region of high homology across the different SCCmec types and one primer in the flanking *Staphylococcus aureus* DNA (Cuny, et al. Clin. Microbiol Infect 2005; 11:834-837, European Patent 1529847 B1). This approach is also subject to false positives as the probability of also priming of MSSA is high with primers encompassing this region.

Finally, a method has been described that positively selects for *Staphylococcus aureus* using specific antibodies and magnetic beads (Francois, et al. Journal of Clinical Microbiology, January 2003, p 254-260; European Patent 1,370,694B1). This approach enriches for *Staphylococcus aureus*, but requires the use of three primer/probe sets to positively identify MRSA and reduces the possibility of detecting CoNS. The method requires a centrifugation step and a separate lysis step to recover the nucleic acid.

The commercially available MRSA assays target the SCCmec right extremity junction and orfX. Five different types and numerous subtypes of SCCmec have been identified and the potential of emergence of new SCCmec subtypes is high. In addition, it is possible that MSSA derived from MRSA might retain part of the SCCmec sequence without the mecA gene. Therefore, assays targeting the SCCmec right extreme junction with orfX are likely to give false positive results with MRSA-derived MSSA and false negative results with MRSA carrying newly emergent SCCmec types/subtypes.

Thus, current methods for detection of MRSA are laborious, time-consuming, and unreliable for routine clinical and surveillance purposes. Accordingly, there exists a need for developing an assay that is fast, easy, reliable and capable of detecting and concurrently distinguishing MRSA from other related bacteria, including MSSA, and/or MR-CoNS.

BRIEF SUMMARY

Embodiments of the present invention relate to systems and methods for detecting methicillin resistant *Staphylococcus aureus* (MRSA) in a sample which may additionally contain methicillin sensitive *Staphylococcus aureus* (MSSA), methicillin resistant coagulase-negative staphylococci (MR-CoNS), and/or other strains of bacteria. Other embodiments of the invention may relate more generically to systems and methods for the analysis of biological entities using plots and boundary functions.

One embodiment of the invention is directed to a method for determining the presence of a biological entity in a sample. The method comprises detecting amounts of at least three genetic elements in the sample. The presence of the biological entity in the sample is determined by executing a call algorithm on a digital computer. The call algorithm uses as inputs the measured values (e.g., amounts) associated with at least three genetic elements and combines them to form a vector, which is compared to a boundary function on a 2-dimensional plot. If the vector is within the boundary function, the biological entity is present and if the vector is not within the boundary function, the biological entity is not present.

Another embodiment of the invention is directed to a system, for determining the presence of a biological entity in a sample. The system comprises a measurement module capable detecting the values (e.g., amounts) of at least three genetic elements in the sample, and a memory storing the detected values (e.g., amounts) from the measurement module. The system also includes a computer readable medium containing computer readable code having instructions for executing a call algorithm, wherein the call algorithm uses as inputs the detected and measured values (e.g., amounts) of the at least three genetic elements and combines them to form a vector. The vector is compared to a boundary function on a 2-dimensional plot. If the vector is within the boundary function, the biological entity is present and if the vector is not within the boundary function, the biological entity is not present. The system also includes a processor to execute the computer readable code on the computer readable medium in order to determine the presence of the biological entity in the sample.

Another embodiment of the invention is directed to a computer readable medium comprising code for a call algorithm. The call algorithm uses as inputs detected and measured values (e.g., amounts) associated with the at least three genetic elements and combines them to form a vector. The vector is compared to a boundary function on a 2-dimensional plot. If the vector is within the boundary function, a biological entity is present and if the vector is not within the boundary function, the biological entity is not present.

Another embodiment of the invention is directed to a method for creating a model that can be used to determine the presence of a biological entity in an unknown sample. The method includes detecting the presence and values (e.g., amounts) of at least three genetic elements in the known samples and executing a call algorithm on a digital computer for each sample in known samples, wherein the call algorithm creates vectors and uses as inputs for each vector the detected values (e.g., amounts) of the at least three genetic elements. Some vectors are associated with the biological entity and some vectors are not associated with the biological entity. The method further includes plotting the vectors on a 2-dimensional plot, and creating a boundary function separating the vectors that are associated with the biological entities and the vectors that are not associated with the biological entity.

According to one embodiment, a method for determining the presence of methicillin-resistant *Staphylococcus aureus* (MRSA) in a sample is disclosed. The method subjects the sample to conditions that will expose the nucleic acids of any bacteria present in the sample. Next, the sample may be amplified and the presence and amounts of at least mecA, SCCmec, and a *Staphylococcus aureus* (SA)-specific target gene sequence in the sample can be detected. The presence of MRSA in the sample can then be determined by executing a call algorithm on a digital computer. The call algorithm may use as inputs the detected and measured amounts of mecA, SCCmec, and the *Staphylococcus aureus*-specific target gene sequence to determine whether MRSA is present in the sample. The call algorithm can be used to determine that MRSA is present in the sample when the detected amounts of mecA, SCCmec, and the *Staphylococcus aureus*-specific target gene sequence in the sample are approximately equal as defined by a selected boundary function.

According to one embodiment, a system for determining the presence of methicillin-resistant *Staphylococcus aureus* (MRSA) in a sample is disclosed. The system may comprise a number of components. For instance, the system may comprise a measurement module that is capable of amplifying and detecting the presence and amounts of at least mecA, SCCmec, and a *Staphylococcus aureus*-specific target gene sequence in the sample after the sample has been subjected to conditions that will expose the nucleic acids of any bacteria present in the sample. The system may further comprise a memory that can store the detected amounts from the measurement module. The system may also comprise a computer readable medium containing computer readable code having instructions for executing a call algorithm. The call algorithm may use as inputs the detected and measured amounts of mecA, SCCmec, and the *Staphylococcus aureus*-specific target gene sequence to determine whether MRSA is present in the sample. The call algorithm can be used to determine that MRSA is present in the sample when the detected amounts of mecA, SCCmec, and the *Staphylococcus aureus*-specific target gene sequence in the sample are approximately equal as defined by a selected boundary function. The system may also comprise a processor that can execute the computer readable code on the computer readable medium in order to determine the presence MRSA in the sample.

According to another embodiment, a computer-readable medium is disclosed. The computer-readable medium may comprise code for a call algorithm that can determine the presence of MRSA in a sample. The call algorithm may use as inputs detected and measured amounts of mecA, SCCmec, and a *Staphylococcus aureus*-specific target gene sequence to determine whether MRSA is present in the sample. The call algorithm can be used to determine that MRSA is present in the sample when the detected amounts of mecA, SCCmec, and the *Staphylococcus aureus*-specific target gene sequence in the sample are approximately equal as defined by a selected boundary function. The detected and measured amounts of mecA, SCCmec, and the *Staphylococcus aureus*-specific target gene sequence can be obtained by subjecting the sample to conditions that will expose the nucleic acids of any bacteria present in the sample and amplifying and detecting the presence and amounts of at least mecA, SCCmec, and the *Staphylococcus aureus*-specific target gene sequence in the sample.

According to yet another embodiment, a method for creating a model that can be used to determine the presence of methicillin-resistant *Staphylococcus aureus* (MRSA) in an unknown sample is disclosed. The method may comprise subjecting a set of known samples to conditions that will expose the nucleic acids of any bacteria present in the known samples. The presence or absence of MRSA is known for each sample in the set of known samples. The method may then amplify and detect the presence and amounts of at least mecA, SCCmec, and a *Staphylococcus aureus*-specific target gene sequence in the known samples. The method may then execute a call algorithm on a digital computer for each sample in the known samples. The call algorithm may use as inputs the detected and measured amounts of mecA, SCCmec, and the *Staphylococcus aureus*-specific target gene sequence. Finally, the method may create a model that can be used to determine whether MRSA is present in the unknown sample. The model can be created from the output of the call algorithm executed against the known samples, and the model can be defined by a selected boundary function that defines a boundary between MRSA-positive and MRSA-negative samples.

These embodiments, as well as other embodiments, will be described in more detail later in this disclosure.

DETAILED DESCRIPTION

Figure 1:
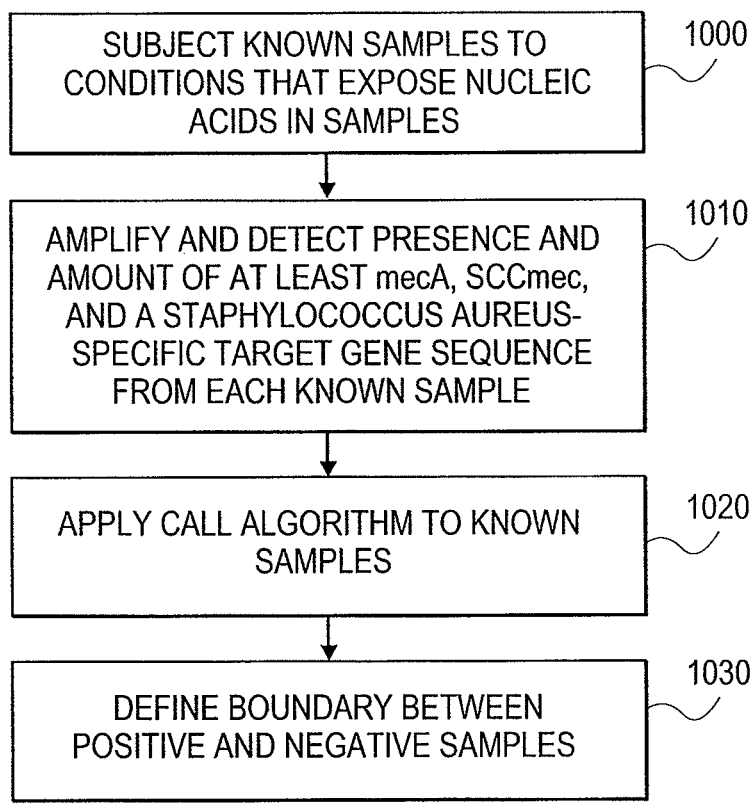
FIG. 1 shows a flowchart illustrating the steps taken in a method according to one embodiment.

Various embodiments disclose systems and methods for identifying Methicillin resistant strains of *Staphylococcus aureus* (MRSA) in a sample that are based on the fact that an MRSA-positive sample can have roughly the same copy numbers of mecA, SCCmec, and a *Staphylococcus aureus*-specific target gene sequence. These systems and methods may further present the three assays simultaneously on a 2-D plot with each axis of the plot 120° angle apart. According to one embodiment, a Y plot is used for the 2-D display. If a given sample has similar values of mecA, SCCmec, and a *Staphylococcus aureus*-specific target gene sequence, the sample's measured copy numbers of mecA, SCCmec, and the *Staphylococcus aureus*-specific target gene sequence can plot very close to the origin regardless of the sample's absolute assay readings. With the help of this transformation, a boundary function can be defined that can be used to distinguish MRSA-positive samples from MRSA-negative samples.

All scientific and technical terms used in this disclosure have meanings commonly used in the art unless otherwise specified. As used in this disclosure, the following words or phrases have the meanings specified.

As used herein, a "boundary function" can be a mathematical function that is used to determine whether data is associated with a biological status or is not associated with a biological status. Boundary functions may be created in any suitable manner including manually, by the use of neural networks, cost functions, etc. Boundary functions may also be represented by any suitable shape or line, including an ellipse, rectangle, circle, or the like. Boundary functions may also be regular or irregular in shape.

As used herein, a "vector" can relate to value derived from one or more components, each component having at least a direction, and typically a scalar.

The term "genetic element" as used herein can refer to a subsequence in a genome of interest that is useful as a target in the methods of the invention. In some embodiments, the genetic element is an open reading frame or gene, such as, for example, orfX, femA or mecA in *Staphylococcus*. A genetic element may also be a mobile genetic element, such as the *Staphylococcus* cassette chromosome, SCCmec, which may or may not comprise the mecA gene.

Herein, the terms "SCCmec" "SCCmec sequence" and "SCCmec cassette" are used interchangeably to refer to the genetic element known as the *Staphylococcus* cassette chromosome, which carries the mecA gene and is inserted into *Staphylococcus* sp. genome as described in Ito et al. (2001, Antimicrob. Agents Chemother. 45:1323-1336).

The SCCmec insertion site is referred to as "orfX-ISS/attBscc" in this application. The insertion site is at the 3' end of a gene referred to herein, as "orfX." The chromosomal locus where SCCmec insertion takes place is referred to as "attBscc." The specific sequence at the insertion site is referred to here as the "orfX-Insertion Site Sequence (orfX-ISS)" or "attBscc core region." This sequence is known to be a highly conserved sequence in *Staphylococcus aureus* (Ito, et al., Antimicrob. Agent Chemother. 2001, 45, p 323-1336, Noto, et al., J. Bacteriol. 2008, 190:1276-1283).

After insertion into the orfX-ISS/attBscc region of *Staphylococcus aureus*, the SCCmec left extremity junction region is referred to as MRSA-LE and the right extremity junction region is referred to as MRSA-RE. In the left extremity junction, the SCCmec sequence is contiguous with the non-orfX side of attBscc. In the right extremity junction, the SCCmec sequence is contiguous with the orfX-side of attBscc. The orfX-ISS/attBscc region is described in detail in Ito et al. (2001, Antimicrob. Agents Chemother. 45:1323-1336; Ito et al., Antimicrob. Agent Chemother. 2004, 48, p 2637-2651, Noto, et al., J. Bacteriol. 2008, 190:1276-1283) and in U.S. Pat. No. 6,156,507, all of which are incorporated by reference herein. If the SCCmec insertion is not present, the orfX-ISS/attBscc region is uninterrupted. If the orfX-ISS/attBscc region is identified as intact through an amplification methodology this indicates that the SCCmec cassette has not been inserted. Lack of amplification of the orfX-ISS/attBscc region, however, does not indicate the mecA gene is present. It is known the mecA gene can be lost after the SCCmec cassette becomes inserted. Thus the SCCmec cassette can still prevent amplification of the orfX-ISS/attBscs region even in the absence of mecA.

An "oligonucleotide" is a nucleotide polymer having two or more nucleotide subunits covalently joined together. Oligonucleotides are generally about 10 to about 100 nucleotides. The sugar groups of the nucleotide subunits may be ribose, deoxyribose, or modified derivatives thereof such as OMe. The nucleotide subunits may be joined by linkages such as phosphodiester linkages, modified linkages or by non-nucleotide moieties that do not prevent hybridization of the oligonucleotide to its complementary target nucleotide sequence. Modified linkages include those in which a standard phosphodiester linkage is replaced with a different linkage, such as a phosphorothioate linkage, a methylphosphonate linkage, or a neutral peptide linkage. Nitrogenous base analogs also may be components of oligonucleotides in accordance with the invention. A "target nucleic acid" is a nucleic acid comprising a target nucleic acid sequence. A "target nucleic acid sequence," "target nucleotide sequence" or "target sequence" is a specific deoxyribonucleotide or ribonucleotide sequence that can be hybridized to a complementary oligonucleotide.

As used herein, the term "probe" refers to an oligonucleotide which is capable of hybridizing to a target nucleic acid of interest. The hybridization occurs as a result of the probe binding through complementary base pairing to a target nucleic acid of interest. It will be understood by one skilled in the art that probes will typically substantially bind target sequences lacking complete complementarity with the probe sequence depending upon the stringency of the hybridization conditions. The probe may be associated with a suitable label or reporter moiety so that the probe (and therefore its target) can be detected, visualized, measured and/or quantitated.

As used herein, the term "primer" refers to an oligonucleotide used to prime nucleic acid synthesis. A primer hybridizes to the template through complementary base pairing and is therefore used to initiate the replication. Hybridization occurs in the same manner as that described for probes, above. In PCR, two primers are used: a "forward primer" that typically hybridizes to the sense strand of a double stranded nucleic acid molecule and a "reverse primer" that typically hybridizes to the antisense strand of the molecule.

As used herein, the term "PCR" refers to a technique for exponential amplification of short DNA sequences (usually 50 to 600 bases) within a longer double stranded DNA molecule by enzymatic replication of DNA without using a living organism (Mullis et al. Methods Enzymol. 1987; 155:335-50). Other in vitro amplification technologies can be used in the present invention and are well known to those of skill. These methods include, for example, Ligase Chain Reaction (LCR), Nucleic Acids Sequence Based Amplification (NASBA), Strand Displacement Amplification (SDA), Transcription Mediated Amplification (TMA), Branched DNA technology (bDNA) and Rolling Circle Amplification Technology (RCAT).

As used herein the term "Real-Time PCR" refers to a type of PCR where the amplified DNA is quantified as it accumulates in the reaction in real time after each amplification cycle (Heid et al, Genome Research, 1996 6(10):986-994). A number of probe chemistries for carrying out Real-Time PCR are well known to those of skill. One commonly used method is the TaqMan® assay (see, e.g., U.S. Pat. Nos. 5,210,015; 5,487,972; and 5,804,375). Other Real-Time PCR probe chemistries that can be used and can be purchased commercially include FRET primers, Molecular Beacons, Scorpion Primers®, Amplifluor Primers®, LUX Primers®, Eclipse®, and Ultimate Probe®. For a review of Real-Time PCR techniques see Bustin et al., *J. Mol. Endocrin.* 34:597-601 (2005).

As used herein, the term "Multiplex PCR" refers to a type of PCR where more than one set of primers is included in a reaction allowing two or more different targets to be amplified in a single reaction tube. The teem "multiplex PCR" also refers to a PCR where multiple primers and probes are used but only one target is amplified. In one embodiment, the multiplex PCR of the present invention is a real-time PCR.

As used herein, a "biological status" may relate to a particular biological state of a sample derived from a patient. In most cases, the biological status relates to whether or not the sample comprises a particular biological entity, for example, a target disease organism or patient cell associated with disease. For example, one biological status may be that a sample comprises MRSA bacteria, while another biological status may be that the sample does not comprise MRSA bacteria. In other examples, the biological status may relate to whether or not the sample comprises cancer cells.

One embodiment of the invention relates to an assay for detection of MRSA in a sample that may contain MRSA, MSSA, MR-CoNS, or other bacteria. Embodiments of the invention utilize a multiplex PCR for simultaneously amplifying and detecting a combination of multiple genetic elements (e.g., targets).

According to one embodiment, the initial amount of target DNA is measured by the PCR threshold cycle (Ct). For example, a defined signal threshold is determined for a reaction to be analyzed. The number of cycles (Ct) required to reach this signal threshold is determined for the target nucleic acid as well as for a reference or standard nucleic acid. The absolute or relative copy numbers of the target molecule can be determined on the basis of the Ct values obtained for the target nucleic acid as compared to the reference nucleic acid. The Ct value is thus inversely proportional to the amount of initial target DNA, see Heid et al, 1996, Genome Research 6(10):986 for a full discussion of the Ct value which is incorporated herein by reference. Other mathematical approaches can be employed which allow for the extrapolation of the initial amount of a particular target gene based upon the indication of a predetermined set amount or number of genes amplified during one of the identified methods.

In one embodiment, the present invention is directed to a method of determining the presence of MRSA in a sample, said method comprising subjecting the sample to real-time PCR for a time and under conditions so as to generate a level of amplification product which is sufficient to be detected by fluorescence and is indicative of an initial level of one or more MRSA-specific target sequences in the sample.

In another embodiment, the amplification is conducted with a set of primers (forward and reverse) and a probe. The probe may be labeled with a fluorogenic reporter molecule at its 5' end and a quenching molecule at its 3' end. The quenching molecule prevents emission of signal from the fluorogenic reporter molecule. The probe hybridizes to a region of the target sequence between the regions to which the forward and reverse primers hybridize. As the polymerase moves along the strand to which the probe has hybridized, the 5' end of the probe is cleaved off by the exonuclease activity of the polymerase thus permitting emission of the fluorogenic signal due to separation of the quenching moiety.

In specific embodiments, the probes of the invention may comprise dual-labeled fluorogenic probes comprising a fluorescent reporter (fluorophore) and a fluorescent or non-fluorescent quencher molecule. The fluorophores of embodiments of the invention may be attached to the probe at any location, including the 5' terminus, the 3' terminus or internal to either termini. In an embodiment of the invention, the fluorophore and quencher are attached to the 5' and 3' termini of the probe respectively. The examples of fluorophores include, but are not limited to, FAM, ROX, HEX, NED, Cy5, Texas Red, Calfluor Red, CalFluor Orange, Quasar 670, Quasar 705. The examples of quenchers include, but are not limited to, TAMARA, Blackhole quenchers BHQ-1, BHQ-2.

In another embodiment, the invention provides a method for detecting and distinguishing MRSA from MSSA, MR-CoNS, or other bacteria utilizing a three target assay, wherein the targets used in the assay include the mecA gene sequence, a *Staphylococcus aureus*-specific target gene sequence, and an SCCmec gene sequence. In a specific embodiment, the *Staphylococcus aureus*-specific target gene is femA. In the descriptions below, femA is often explicitly mentioned as the *Staphylococcus aureus*-specific target gene sequence; however, other *Staphylococcus aureus*-specific target gene sequences may also be used according to various embodiments. Yet other targets that can be used to determine the presence of MRSA can include orfX.

Various embodiments need not use traditional positive-negative or delta approaches in order to determine the presence of MRSA. Instead, an approach is used that is based on the fact that an MRSA positive sample has roughly the same copy numbers of mecA, femA, and SCCmec. When the copy numbers of mecA, femA, and SCCmec are present in roughly equal amounts, it can be indicative of the presence of MRSA in the sample. In embodiments of the invention, the Ct values of mecA, SCCmec, and femA can be analyzed using an assay call algorithm. This call algorithm may further present the three assays simultaneously in a 2-D plot with lines 120 degrees apart. This plot can be referred to as a Y-plot since each of the three axes of the plot, representing the measured amounts of mecA, SCCmec, and femA, appear as a "Y" on a 2-D plot. If a sample has similar readings of mecA, femA, and SCCmec, the sample's measured copy numbers of mecA, femA, and SCCmec will plot close to the origin of the plot regardless of the sample's absolute assay readings. With the help of this transformation, a rectangle gating approach may be sufficient to distinguish MRSA positive and negative samples. Other suitable approaches may use a circular gating process, a neural network, or a Gaussian distribution function. Additional details are provided below.

FIG. 1 illustrates steps that can be used to build a model that can be used to determine whether MRSA is present in a sample according to one embodiment. A boundary function in the model can separate MRSA-positive samples from MRSA-negative samples based on the measured amounts of mecA, SCCmec, and a *Staphylococcus aureus*-specific target gene sequence.

In more general terms, one embodiment of the invention is directed to a method for creating a model that can be used to determine the presence of a biological entity in an unknown sample. The method includes detecting the presence and amounts of at least three targets in the known samples and executing a call algorithm on a digital computer for each sample in known samples, wherein the call algorithm creates vectors and uses as inputs for each vector the detected amounts of the at least three targets. Some vectors are associated with the biological entity and some vectors are not associated with the biological entity. The method further includes plotting the vectors on a 2-dimensional plot, and creating a boundary function separating the vectors that are associated with the biological entities and the vectors that are not associated with the biological entity.

At step 1000, a selected number of known samples are subjected to conditions that expose the nucleic acids of bacteria in the samples. In this context, a known sample is a sample in which it is already known whether the sample should test positive or negative for MRSA. The known samples can thus be used to build a model that can determine whether a later unknown sample also contains MRSA. Although MRSA is described in detail, it is understood that the presence of other suitable biological entities could be detected in other embodiments of the invention.

There are many different ways for subjecting a sample to conditions that expose the nucleic acids in the sample. For example, as it is well-known in the art, a sample may have its temperature raised to separate strands of DNA. Other well-known means for exposing the nucleic acids in a sample may also be used.

At step 1010, the presence and amounts of at least three targets, such as mecA, SCCmec, and a *Staphylococcus aureus*-specific target gene sequence, are detected for each of the known samples. In some embodiments, Ct values may be measured for each of the targets of interest. According to one embodiment, the *Staphylococcus aureus*-specific target gene sequence is femA. There are many different ways to measure the genes from a sample. For example, a multiplex PCR can be used to measure the PCR threshold cycle (Ct) for each target of the measurement. Other measurement techniques may also be used.

The determined Ct values can be used to create a Y-Plot. However, prior to the creation of the Y-Plot, a pre-screening process can be carried out. In the prescreening process, if the system does not detect any of three target gene sequences, the sample is deemed MRSA negative and will not be shown in the Y-Plot. In one embodiment, a sample is deemed negative if mecA>35, femA>32, or SCCmec>32. In another embodiment, a sample is deemed negative if mecA>30, femA>30, or SCCmec>30. In some embodiments, the sample will be plotted on and analyzed with the Y-Plot after it survives this prescreening process. The thresholds used in the prescreening process can be dependent on instrument and sample preparation.

At step 1020, a call algorithm can be applied to each of the measured targets from each of the known samples. According to one embodiment, the call algorithm may use a Y plot.

According to one embodiment, for each known sample, the call algorithm creates an intermediate vector that can be projected onto a 2-D plot, which may be a Y_plot. The intermediate vector may be the sum of three unit vectors 120 degrees apart from each other and weighted by the mecA, femA, and SCCmec values taken from step 1020. According to one embodiment, the sum of the vectors can be represented by the formula:

$$\vec{p} = mecA * e^{0i} + femA * e^{\frac{2}{3}\pi i} + SCCmec * e^{\frac{4}{3}\pi i},$$

where $\vec{p}$ is the intermediate vector. femA may be replaced by the generic variable "SA" (representing a value associated with a *Staphylococcus aureus*-specific target gene sequence). Other similar means for representing how the relative amounts of the measured targets may also be used according to other embodiments.

At step 1030, the intermediate vectors created during step 1020 for each known sample can be analyzed in order to create a model that can be used to determine whether unknown samples contain MRSA. According to one embodiment, a boundary function is selected and the parameters of the boundary function are defined using the intermediate vectors of the known samples. The boundary function can be used to determine if MRSA is in an unknown sample or is not in an unknown sample.

According to one embodiment, a clustering analysis can be performed on a Y plot of all of the measured known samples to separate MRSA positive and negative samples. A clustering analysis can group positive samples together because femA, mecA, and SCCmec are single copy targets and there should be equal copies of these targets in MRSA positive samples. Mathematically, this means if a sample is MRSA positive, then its intermediate vector on Y plot should be near the origin. Thus, a simple boundary function, such as a rectangular area that encompasses the positive samples, can be used to cluster the positive samples that are located around the origin of the Y plot. The negative samples may be scattered outside of this boundary. According to one embodiment, a simple rectangular box can be used to separate positive and negative samples on the Y plot. The boundaries of the rectangular box can be adjusted using the measurements from the known samples. For example, a neural network algorithm could be used to help define the boundaries of the box. Other embodiments may select more complicated boundary functions or use other means to adjust the coefficients of the selected boundary function. As noted above, boundary functions can be created using other approaches (e.g., a circular gating process, a neural network, or a Gaussian distribution function).

Figure 2:
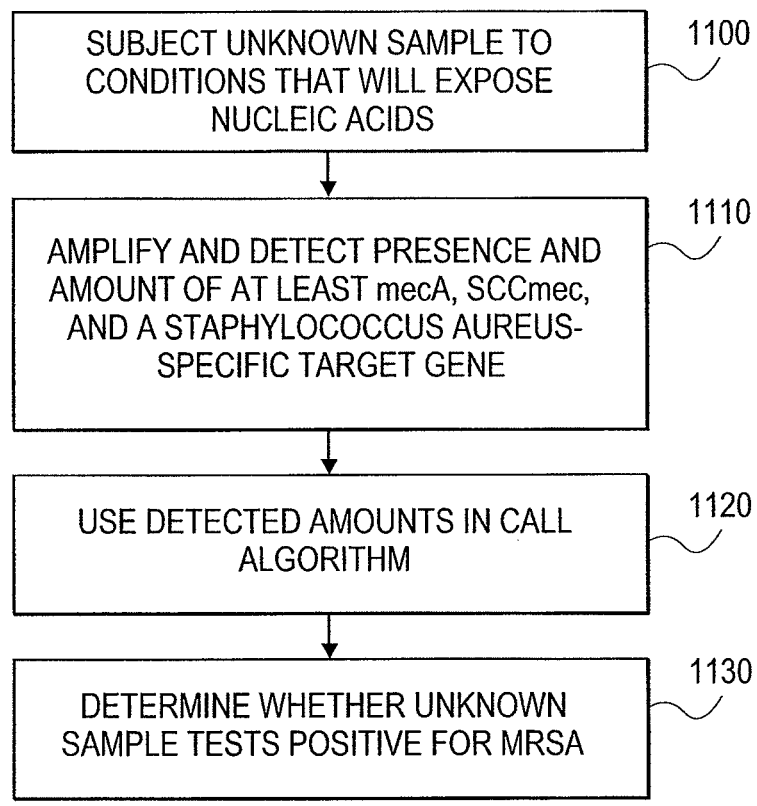
FIG. 2 shows a flowchart illustrating the steps taken in a method according to one embodiment of the invention.

FIG. 2 illustrates steps that can be used to determine whether MRSA is present in a sample according to one embodiment. As used herein, an unknown sample refers to a sample in which it is not known whether MRSA is present in the sample. The steps in FIG. 2 can use a model, such as a model created using the steps from FIG. 1, to determine whether an unknown sample contains MRSA. The unknown sample can have various targets measured, and these measurements can be used to detect the presence of MRSA by analyzing where an intermediate vector created from the measured targets of the unknown sample resides relative to a boundary function of the model.

In more general terms, an embodiment of the invention is directed to a method for determining the presence of a biological entity in a sample. The method comprises detecting values (e.g., amounts) of at least three targets in the sample. The presence of the biological entity in the sample is determined by executing a call algorithm on a digital computer. The call algorithm uses as inputs the measured values (e.g., amounts) of at least three targets and combines them to form a vector, which is compared to a boundary function on a 2-dimensional plot. If the vector is within the boundary function, the biological entity is present and if the vector is not within the boundary function, the biological entity is not present.

At step 1100, the unknown sample is subjected to conditions that expose the nucleic acids of bacteria in the sample. The same techniques used during step 1000 while building the model can also be used at step 1100.

At step 1110, the Ct values at least three targets, mecA, SCCmec, and a *Staphylococcus aureus*-specific target gene sequence, are measured from the unknown sample. The same techniques used during step 1010 can be used to accomplish step 1110.

At this point, a similar pre-screening process, as described above, can be used to remove samples that are very likely to not be associated with MRSA.

At step 1120, the call algorithm used to build the model can be applied to the measured targets from unknown sample. For example, an intermediate vector can be created from the unknown sample using the same function that was used at step 1020.

At step 1130, it is determined whether MRSA is present in the unknown sample. According to one embodiment, this can be accomplished by comparing the intermediate vector created for the unknown sample against the boundary function created from the known samples. If the intermediate vector for the unknown sample falls within the boundary that designates positive MRSA samples, then it can be determined that MRSA is present in the unknown sample. If the intermediate vector for the unknown sample falls outside of the positive MRSA boundary, then it can be determined that MRSA is not present in the unknown sample.

Embodiments of the invention are particularly advantageous. As noted below, embodiments of the invention are particularly useful in identifying MRSA in a sample, despite the fact that MRSA can often co-colonize with multiple other related bacteria.

The various embodiments of the invention are demonstrated further by the following illustrative examples. The examples are offered by way of illustration and are not intended to limit the invention in any manner.

Illustrative Example 1

Sample Preparation 659 samples were collected and analyzed to form a model that can be used according to one embodiment. The samples were known samples, i.e., it was known whether MRSA was present in each of the samples. Two swabs were collected for each sample. These two swabs were then cultured for MRSA independently. If the culture results from two swabs agree, this sample was considered valid.

Each valid known sample was then placed in a sample buffer tube with 1 ml of Tris, pH 8.0 and 1 mM EDTA, pH 8.0. The sample buffer tube was vortexed for 40 seconds at 3000 rpm to dislodge bacteria from the swab head. 500 μL of the bacterial suspension (i.e., the sample buffer containing bacterial suspension) was then transferred into a new tube.

10 μL of Process Control Working Stock was then added to the new tubes. 10 μL of cell wall digesting enzyme was also added to the new tubes. After a brief vortex, the tubes were incubated at 70° C. for 5 minutes. Bacterial DNA was then extracted using the Agencourt VirNA Extraction Kit.

A pre-mix was then prepared by mixing together 188 μL of lysis buffer, 1.0 μl of polyA RNA (10 μg/μl), and 100 μl of Proteinase K (20 mg/ml) (in 10 mM Tris pH 8.0, 50% glycerol, 5 mM calcium chloride).

The pre-mix was then added to the tubes, vortexed for 10 seconds at 1700 RPM, and then incubated in a 70° C. water bath for 5 minutes.

After the tubes were cooled to room temperature, 575 μL of 100% isopropanol and 10 μL of binding buffer (paramagnetic beads coated with carboxyl groups) were added to the tubes, and the tubes were vortexed for 10 seconds at 1700 RPM.

The tubes were then incubated at room temperature for 2 minutes and then placed on a microcentrifuge tube magnet for 6 minutes to capture the magnetic beads. The supernatant was aspirated off without disturbing the magnetic beads. The tubes were then taken off the magnet and 500 μL of Wash Buffer (3.3M Guanidine thiocyanate, 1.7% v/v Triton X-100, 167.5 mM sodium citrate) was added.

The tubes were vortexed for 10 seconds at 1700 RPM then placed back on the magnet for 4 minutes. The supernatant was aspirated off and discarded. The tubes were taken off the magnet and 900 μL of 75% ethanol was added. The tubes were then vortexed for 10 seconds at 1700 RPM, placed back on the magnet for 6 minutes, and the supernatant was aspirated off. The 75% ethanol wash was repeated for a total of two washes. The magnetic beads were allowed to dry on the magnet for 15 minutes at room temperature.

To elute the DNA, 25 μL of nuclease free water was added to the dried beads. The tubes were vortexed briefly and then incubated at 70° C. for 5 minutes. The tubes were then placed back on magnet for 1 minute. The eluted nucleic acid was used for PCR analysis.

PCR Reaction Mix Setup

PCR reagents were first thawed and then maintained on ice during the following steps. Edge wells were not used on a 96-well plate (Rows A and H, columns 1 and 12). One positive and 1 negative control were used per PCR plate.

A reaction mix was then prepared for the required quantity of samples and control. The reaction mix was prepared based on increments of 12 reactions.

The following volumes were added to a 2.0 ml polypropylene tube: 300 μL of 5×PCR Reaction Buffer (required volume per reaction*13), 108.33 μL of 6× Oligo Mix (required volume per reaction*13), 2.6 μL of 1M MgCl2 (required volume per reaction*13), 31.2 μL of 1 unit/μl UDG (required volume per reaction*13), 20.8 μl of 12.5 mM dNTPs (required volume per reaction*13), 1.82 μL of 40 unit/μl DNA polymerase (required volume per reaction*13), and 95.25 μL H2O (required volume per reaction*13).

The reaction mix was aliquoted into a Stratagene 96-well PCR plate at a volume of 30 μL per well. 20 μL of SPRI-TE extracted DNA sample was added to a single well. 20 μL of Negative Control was added to a single well with nuclease free water. 20 μL of Positive Control was added to a single well. The sample and reaction mix was then created by pipetting the mixture up and down 10 times, using a pipette set at 45 μL. The prepared PCR plate was then sealed with an Optical Adhesive Cover and then centrifuged at 3000 rpm for 3 minutes.

Model Creation and Analysis

The plate was then loaded onto a Stratagene Mx3005P qPCR instrument. The used wells in the plate were selected and the following dyes were selected for fluorescence data collection: CY5, HEX, ROX, FAM. Finally, the following cycling conditions were specified: 4' @ 37° C. (1×); 1' @ 95° C. (1×); 5" @ 91° C.→10" @62° C.→25" @ 58° C. (50×). Some of the targets monitored are represented in Table 1 below.

TABLE 1

| | | | |
|---|---|---|---|
| femA | Forward primer | femA-3 forward primer | GACCGTTATAATTTCTATGGTGTTAGTGG (1) |
| | Reverse primer | femA-3 reverse primer | GTCACCAACATATTCAATAATTTCAGC (2) |
| | TaqMan probe | femA-sa-probe | ACAGAAGATGCTGAAGATGCTGGTGT (3) |
| mecA | Forward primer | mecA-2 forward primer | GCAGAAAGACCAAAGCATACATATTGA (4) |
| | Reverse primer | MecA-2 reverse primer | GCCTATCTCATATGCTGTTCCTGT (5) |
| | TaqMan probe | mecAprobe | AGACCGAAACAATGTGGAATTGGCCA (6) |
| S.felis (IC) | IC forward primer | Sfforwardnew | TGCCAATGTAGATAGTCTTCCAGA (7) |
| | IC reverse primer | sfreversenew | AAGTGCCCAGAAGAATGAGTGG (8) |
| | IC probe | fSfelis | ACCGCCACCATTATTACGTACAGCTG (9) |
| SCCmec | Forward primer | OrfX-ISS/attBScc for-1 | TGAGGGTTGTGTTAATTGAGCAAGTG (10) |
| | Forward primer | OrfX-ISS/attBScc for-2 | TGCGGGTTGTGTTAATTGAACAAGTG (11) |
| | Reverse primer | mecII512-1-sccmec-3 | TCACTTTTTATTCTTCAAAGATTTGAGC (12) |
| | Reverse primer | primer11-1-sccmec-7 | AAATTGCTACTAAAGAGGATATGGAAAACCATC (13) |
| | Reverse primer | primer12-sccmec-8 | CTCTGCTTTATATTATAAAATTACGGCTG (14) |
| | Reverse primer | newtypeiii-1-sccmec-14 | CGTATGATATTGCAAGGTATAATCCAATATTTC (15) |
| | Reverse primer | typeIVc-sccmec-2 | CTTGAAATGAAAGACTGCGGAGGCTAAC (16) |
| | Reverse primer | NEWPRIMERS | TGAGCTTTTTCCACTCCCATTTCTTCCAAA (17) |
| | Reverse primer | SCCmec-4nV | GCAATTCACATAAACCTCATATGTTCTGATAC (18) |
| | Reverse primer | SCCmec-3n | CATTCATTCATCCACCCTAAACTTAATCTTTC (19) |
| | Reverse primer | SCCmec-5n | TATGGAAATCCATCTCTACTTTATTGTTTTCTTC (20) |
| | Reverse primer | SCCmec-6n | AATATTTCATATATGTAATTCCTCCACATCTC (21) |
| | Reverse primer | SE-7-11 | CTATTTCTGTAATACTTAAAACCTTTTCTTCC (22) |
| | Reverse primer | SE-17 | CCGTATGATTCATATTAAAATGAATCATACGGAGG (23) |
| | Reverse primer | SE-13 | CTTCTTATGAAATGTCTTTTTTCACTTATCC (24) |
| | TaqMan probe | orfx probe-2 | ATGCTTCTCCTCGCATAATCTTAAAYGCTC (25) |
| | TaqMan probe | ORFX PROBE-1 | ACGCTTCTCCACGCATAATCTTAAATGCTC (26) |
| | TaqMan probe | ORFX PROBE | ACGCCTCTCCTCGCATAATCTTAAATGCTC (27) |

In the table above, the probes for SCCmec have sequences that are complementary to the right extremity of SCCmec.

In other embodiments, other primers and probes that are substantially identical in sequence and/or length can be used in embodiments of the invention.

First, all sample wells and the positive control well were selected along with a threshold value. A data analysis is then conducted. The PCR threshold values, in the order of FAM, HEX, ROX, and CY5, were then recorded and placed into an assay call algorithm file. The collected threshold values for the samples correspond to the amount of mecA, femA, and SCCmec in each of the samples.

As with the embodiment illustrated in FIG. 1, an intermediate vector was created for each sample. Each intermediate vector was the sum of three unit vectors 120 degrees apart from each other and weighted by mecA, femA, and SCCmec values respectively. The formula used was:

$$\vec{p} = mecA * e^{0i} + femA * e^{\frac{2}{3}\pi i} + SCCmec * e^{\frac{4}{3}\pi i},$$

where $\vec{p}$ is the intermediate vector. An illustration of the how some of these samples appear when plotted on a 2-D Y plot is shown in FIG. 3.

Figure 3:
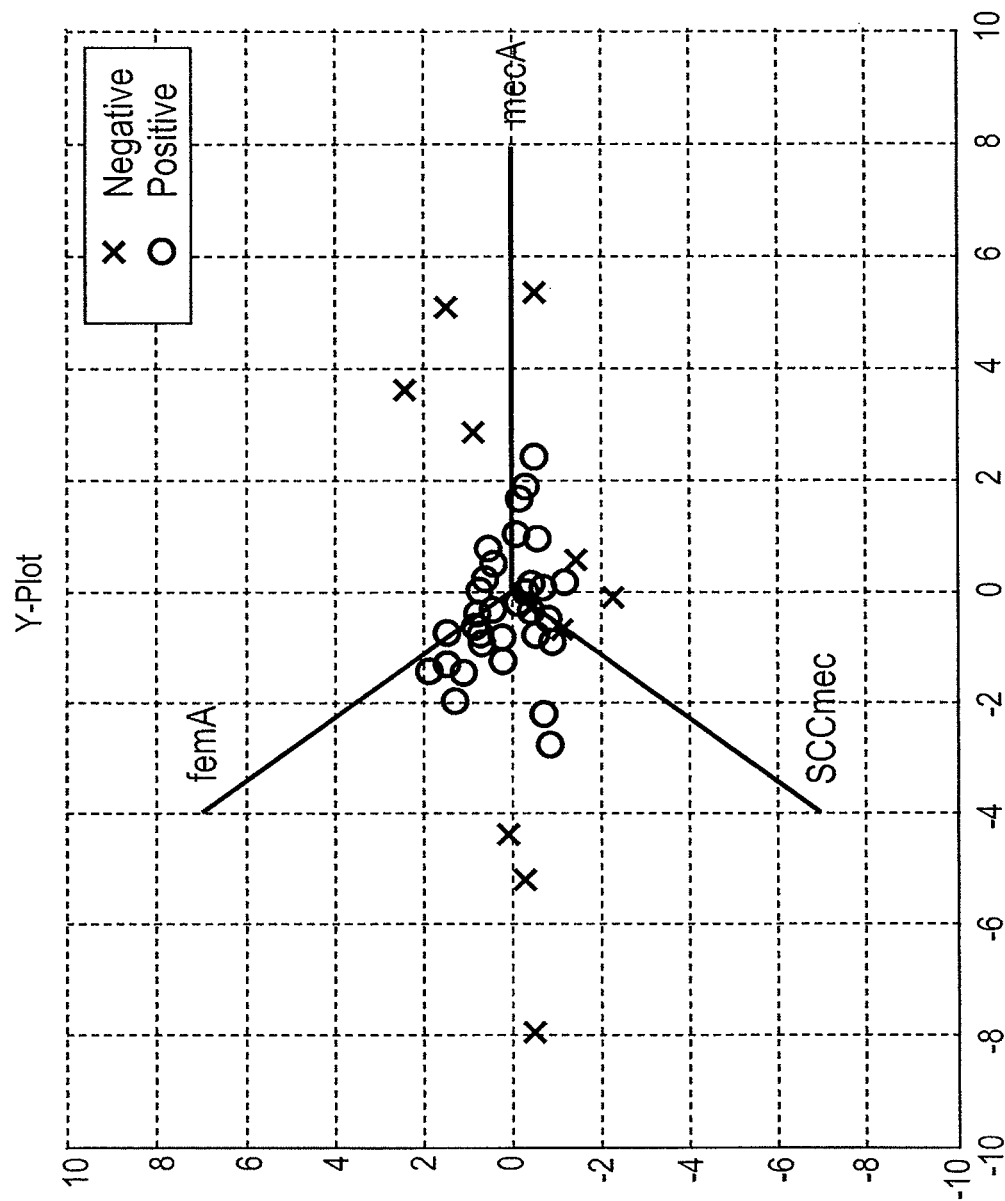
FIGS. 3-5 show diagrams illustrating the outputs of call algorithms from various positive and negative samples according to embodiments of the invention.

As can be seen in FIG. 3, the intermediate vectors created from the MRSA positive samples generally have their endpoints clustered around the origin of the plot. In contrast, the MRSA negative samples generally have the endpoint of their intermediate vectors residing at locations more distant from the origin.

Figure 4:
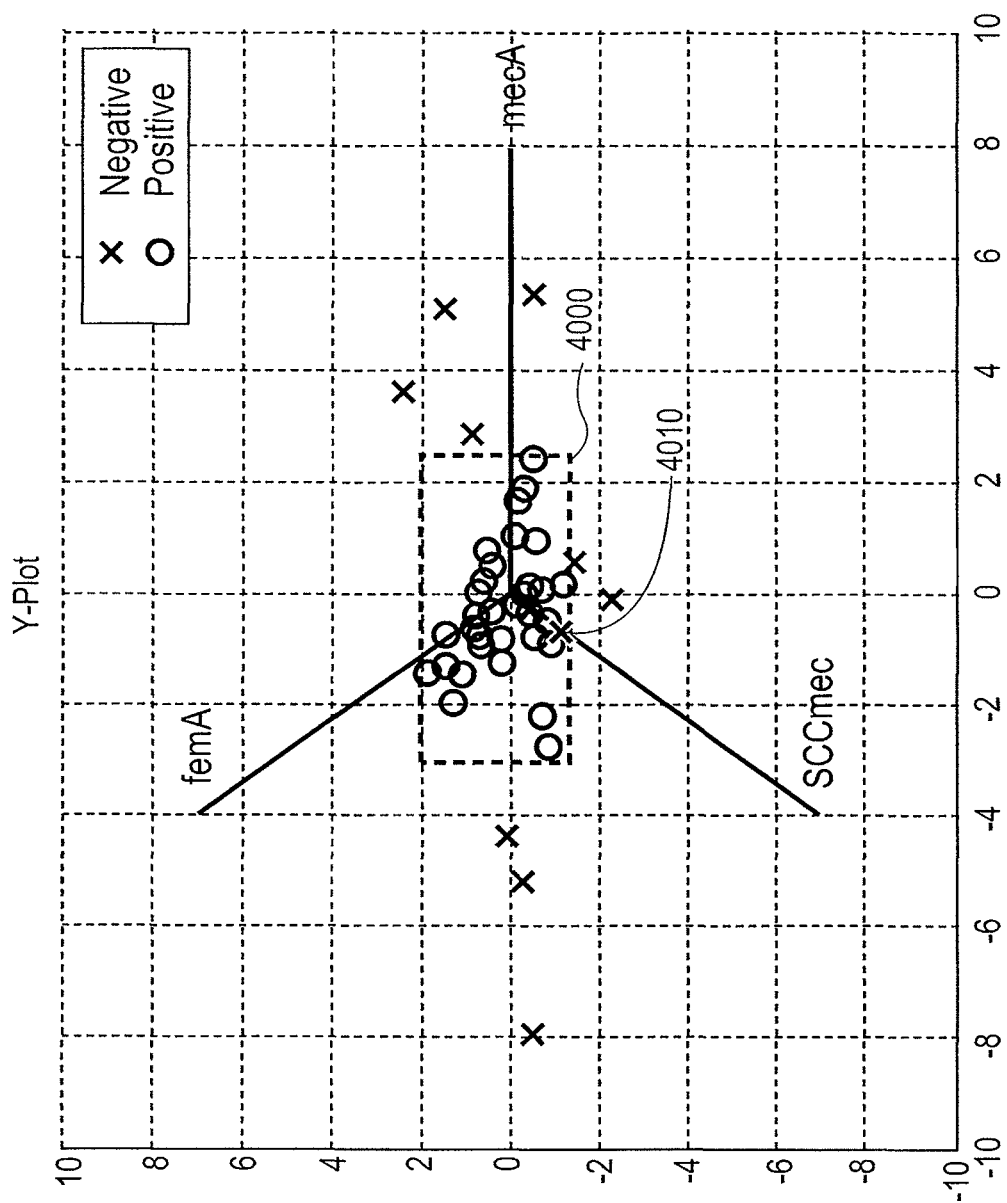

FIG. 4 shows how a simple rectangle box 4000 can be used as a boundary function to separate positive and negative samples. Using the 659 samples as the basis for the model, the left, right, top, and bottom edges of the rectangle box are at −3, 2.5, 2, and −1.3. Rather than using a simple rectangle to cluster the samples, more sophisticated methods may be applied for other models. For example, the boundary may be defined by a function that is then tuned using a neural network. Also, the boundary does not need to rectangular; more complicated geometries may yield better fits to the known samples in other models.

The known samples can then be analyzed using the newly created model to test how accurately the model categorizes the known samples. A Y-plot-based call algorithm that computes an intermediate vector for each known sample and compares the vector with the boundary function, as described above, resulted in 5 false negatives (FN's) and 0 false positives (FP's) for the 659 samples. A closer look at the 5 FN's revealed that 3 out of 5 samples had at least one assay without a Ct value (Ct=40). This should not happen with positive samples. For this reason, these 3 samples are not considered to be reliable test points. Thus, after removing these 3 FN's, there are 2 FN's and 0 FP left. One of these false negatives is highlighted in FIG. 4 at 4010.

In contrast, a reference method (BD Geneohm™ MRSA assay) applied to the known samples resulted in 3 FN's and 9 FP. Thus, the new MRSA call algorithm show significant reduction in FP's without increasing FN's as compared to the reference method.

Illustrative Example 2

Sample Preparation

199 Nasal swabs were collected and stored in a Stuart transport medium. The swab heads were removed and each swab head was transferred into a 2 ml sample suspension tube with 1200 μL of Tris based sample buffer with 10 mM Tris pH 8.0 and 1 mM EDTA, pH 8.0~100 mg of 1 mm Zirconia/Silica beads. The bacteria on the swab heads were dislodged by vortexing the sample tubes at speed of 3000 rpm for at least 15 seconds.

The swab heads were then sterilely removed from the sample tubes and transferred into 15 ml bacteria culture tubes with 1 ml of Trypic Soy broth (TSB) and 6.5% NaCl. The inoculated bacteria tubes were transferred into a 37° C. incubator and incubated overnight with shaking at speed of 200 rpm.

The presence or absence of *Staphylococcus aureus* and/or MRSA was then confirmed. 10 μL of each of the overnight culture broths was streaked on BBL™ CHROMagar MRSA and a BBL™ CHROMagar *Staphylococcus aureus* plate. 500 μL of the 1200 μL sample solution from each tube was then subjected to DNA isolation procedure as described by Agencourt VirNA kit protocol. This procedure, in brief, began with an amount of CFU *S. felis* bacteria (or an amount of *S. felis* without CFU) as a process control. 10 units of Achrompeptidase were added to each tube, mixed well, and incubated in a 70° C. waterbath for 4 minutes. 289 μL of a freshly prepared lysis solution containing 188 μL of a lysis buffer, 1.0 μL of PolyA (600 ug/ml), and 100 μL of protease K (6.4 mg/ml) was then added to each sample and mixed well. Each sample was then incubated and then allowed to cool for 2 minutes. Then, 10 μL of magnetic beads and 575 μL of 100% isopropanol were added and mixed well by vortexing. The reaction contents were allowed to incubate at room temperature for 5 minutes, and then the magnetic beads were collected by placing the sample tube on a magnet stand for 6 minutes to separate the magnetic beads from the sample solution until the solution become clear.

Next, the supernatant was aspirated off the samples while being careful not to remove any beads during aspiration. 500 μL of washing buffer were added to the samples and vortexed for 10 seconds to mix. The tubes were then incubated on the magnet for 4 minutes (or until clear). The supernatant was then aspirated off the samples again. 900 μL of freshly prepared 75% ethanol was then added and the tube vortexed for 10 seconds. The tubes were then incubated on the magnet for 4 minutes until clear. The supernatant was then aspirated off the samples again and the ethanol washing was repeated one more time. The beads were then dried on the magnet for 15-25 minutes. When the ring of the beads started to crack, the sample was eluted. The tubes were taken off the magnet and 25 μL of nuclease free water was added to elute the DNA. The samples were then vortexed to mix. The tubes were then incubated for 5 minutes at 70° C. The tubes were placed back on the magnet and incubated for 1 minute. The eluate was then transferred to a clean tube for PCR amplification.

PCR Primers and Probes, PCR Cycling Conditions

The reagents listed in the Master mix table were prepared on ice. According to the total reaction number, enough Master mix can be prepared by simply adding the indicated volumes of reagents together in a DNA/RNase-free tube. The tubes can be vortexed to mix and then left on ice for later use. 20 μL of each eluate was added to a Mx3000P 96-well PCR plate (non-skirted) (Stratagene, Cat#401333) (one eluate, one well). 30 μL Master mix was added to each well filled with the eluate, and then mixed by gently pipetting up and down 8 times or more (a multi-channel might be useful). The plate was covered tightly with MicroAmp™ optical adhesive film (Applied Biosystems), and then centrifuged at 1100×g for 3 minutes before it is put into the PCR machine.

The PCR cycling conditions on the Stratagene MX3005P instrument were set as follows: 4' @ 37° C. (1×); 1 min @ 95° C. (1×); 15 sec @ 95° C.→10 sec @62° C.→30 sec @ 58° C. (40×). Some targets that were monitored are described above.

Model Creation and Analysis

The threshold values of each target are exported and input into a call algorithm as previously described with the first illustrative example.

Figure 5:
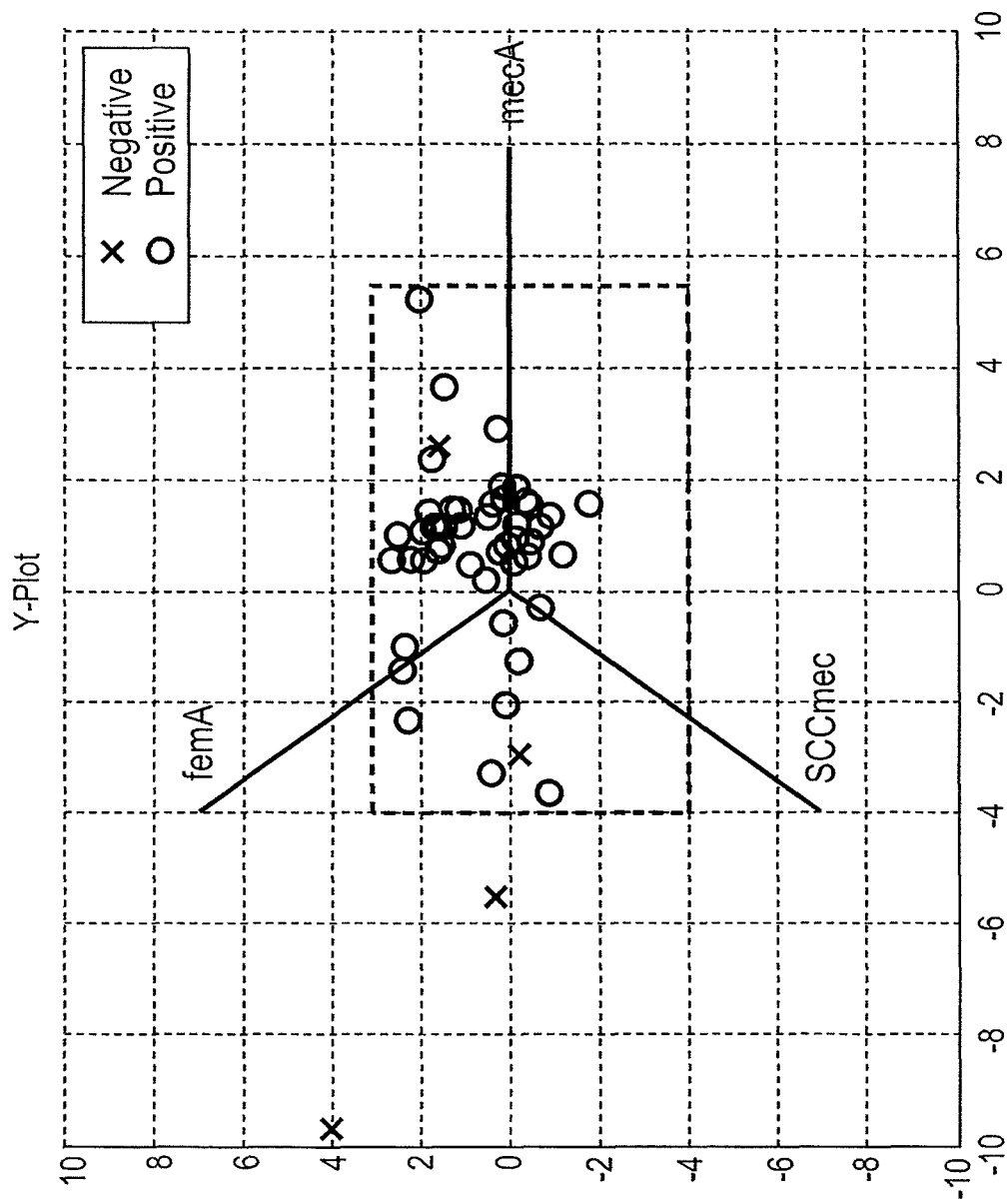

Since the known samples in this example were not collected in exactly same way as the first example, the left, right, top, and bottom edged of the rectangle box in Y-Plot algorithm for the second example were found to be −4, 5.5, 3, and −4. This is illustrated in FIG. 5. When the known samples were re-processed using the model, 3 false positives and 4 false negatives were found. This represented an improvement over a Cephied Xpert® MRSA reference method which yielded 11 false positives and 2 false negatives.

Figure 6:
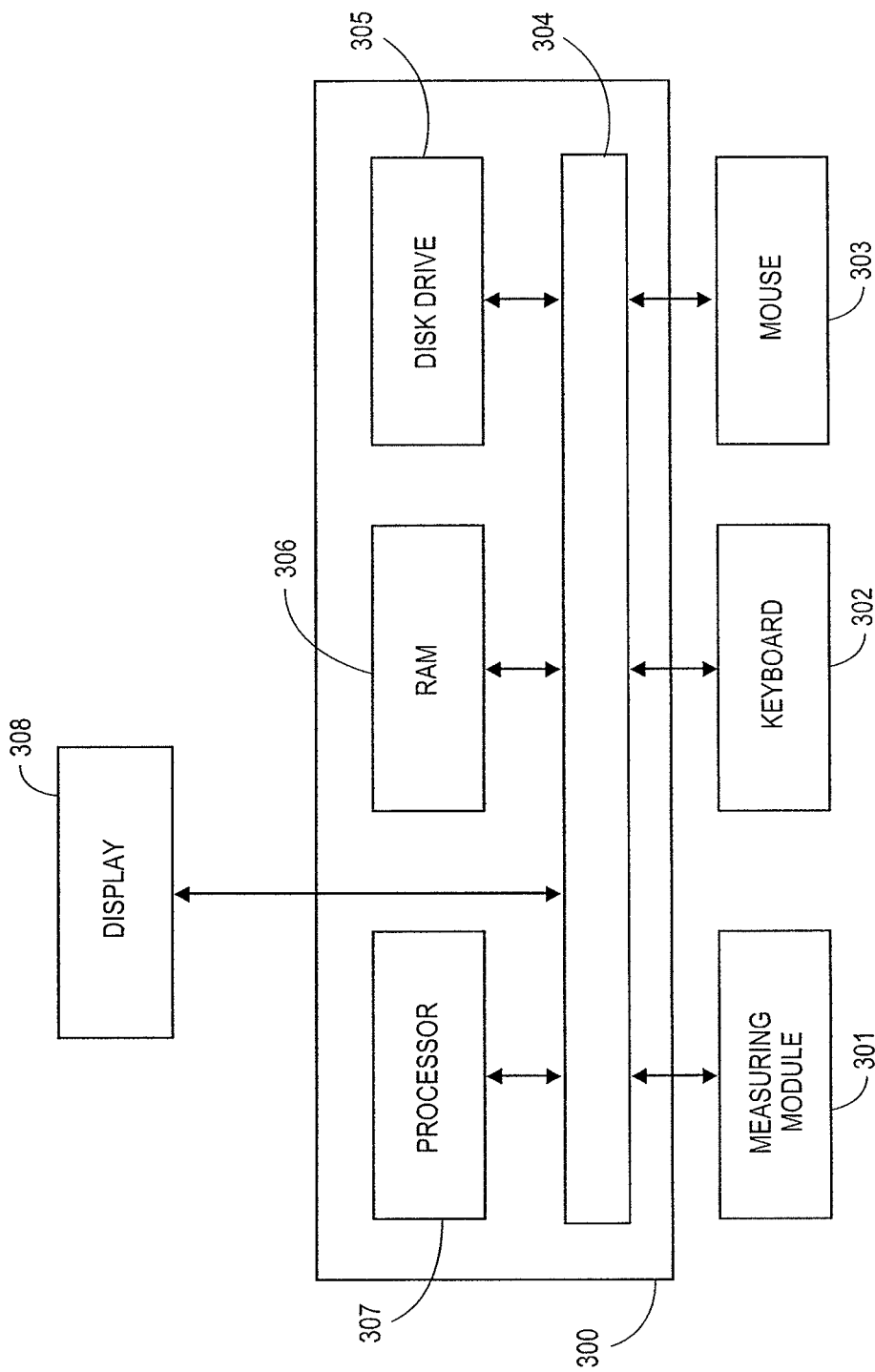
FIG. 6 is a block diagram of a system that can be used to execute various embodiments of the invention.

FIG. 6 is a block diagram of a computer system 300 that can be used to execute one embodiment of the invention. The computer system 300 has a number of input modules. A measurement module 301 is used to measure selected targets in a sample. This measurement module may vary between different embodiments of the invention depending on the measurement method selected to measure the target responses. For example, according to one embodiment, the measurement module may conduct a PCR analysis on a sample. The measurement module may be embodied by at least part of the working components of a typical real time PCR apparatus. Also shown are a standard keyboard 302 and mouse 303. The computer system 300 also contains a variety of typical computer components inside the computer. These components include a system bus 304, one or more disk drives 305, RAM 306, and a processor 307. Other components can also be present depending on the exact nature of the embodiment. FIG. 5 also shows a monitor 308 that allows information to be displayed to a user of the system.

In one embodiment of the invention, a sample is placed in the measurement module 301 where the sample is processed and amounts of the selected targets from the sample are measured. This information is then transferred into the computer system along a system bus 304, and an appropriate call algorithm can be applied to the response data using the processor 307. The instructions the processor 307 executes to implement the call algorithm are stored on a computer readable medium such as the RAM 306 or disk drive 305. The call algorithm can also be stored on this same media. The output of the call algorithm can then be displayed on the monitor 308. For example, if the call algorithm uses a 2-D Y plot to graph the measured amounts of three targets via an intermediate vector, the end point of the intermediate vector can be displayed on the monitor 308. Alternative embodiments of the invention can output information via other communications means. For example, the computer system could print the Y plot using a printer or send the Y plot to another computer over a network. The information from the measured sample can then be used to either help build a model or determine whether the sample contains MRSA.

As will be apparent to those skilled in the art to which the invention pertains, the present invention may be embodied in forms other than those specifically disclosed above without departing from the spirit or essential characteristics of the invention. The particular embodiments of the invention described above, are, therefore, to be considered as illustrative and not restrictive. The scope of the present invention is as set forth in the appended claims rather than being limited to the examples contained in the foregoing description.

The software components, steps, or functions described in this application, may be implemented as software code to be executed by one or more processors using any suitable computer language such as, for example, Java, C++ or Perl using, for example, conventional or object-oriented techniques. The software code may be stored as a series of instructions, or commands on a computer readable medium (e.g., a non-transitory computer readable medium), such as a random access memory (RAM), a read only memory (ROM), a magnetic medium such as a hard-drive or a floppy disk, or an optical medium such as a CD-ROM. Any such computer readable medium may also reside on or within a single computational apparatus, and may be present on or within different computational apparatuses within a system or network.

Some embodiments of the present invention can be implemented in the form of control logic in software or hardware or a combination of both. The control logic may be stored in an information storage medium as a plurality of instructions adapted to direct an information processing device to perform a set of steps disclosed in an embodiment of the present invention. Based on the disclosure and teachings provided herein, a person of ordinary skill in the art will appreciate other ways and/or methods to implement the present invention.

Any recitation of "a", "an" or "the" is intended to mean "one or more" unless specifically indicated to the contrary.

REFERENCES

K. Becker, I. Pagnier et. al. Does nasal cocolonization by Methicillin-resistant coagulase-negative staphylococci and methicillin-susceptible *Staphylococcus aureus* strains occur frequently enough to represent a risk of false-positive methicillin-resistant *S. aureus* determination by molecular methods? Journal of Clinical Microbiology, January 2006, p 229-231.

C. Cuny and W. Witte. PCR for the identification of Methicillin-resistant *Staphylococcus aureus* (MRSA) strains using a single primer pair specific for SCCmec elements and the neighbouring chromosome-borne orfX. Clin. Microbiol Infect 2005; 11:834-837.

C. Cuny and W. Witte. Method for detecting methicillin resistant *Staphylococcus aureus* (MRSA). European Patent Application EP 1529847 A1, Nov. 5, 2005.

P Francois, D. Pittet et. al. Rapid detection of Methicillin-resistant *Staphylococcus aureus* directly from sterile or nonsterile clinical samples by a new molecular assay. Journal of Clinical Microbiology, January 2003, p 254-260.

K. Hiramatsu, T. Ito et. al. Method of identifying methicillin-resistant *Staphylococcus aureus* or methicillin-resistant coagulase negative staphylococci. U.S. Pat. No. 6,156,507, Dec. 5, 2000.

A. Huletsky, R. Giroux et. al. New real time PCR assays for rapid detection of methicillin-resistant *Staphylococcus aureus* directly from specimens containing a mixture of staphylococci. Journal of Clinical Microbiology, May 2004, p 1875-1884.

H. Matsunaga, K. Tsukumo et. al. Method and kit for detecting methicillin resistant *Staphylococcus aureus*. U.S. Pat. No. 5,702,895, Dec. 30, 1997.

J. Schrenzel and P. Francois. Method for direct detection of methicillin-resistant *Staphylococcus aureus*. United States patent Application Publication US2004/0241824 A1, Dec. 2, 2004.

D. Sinsimer, S. Leekha et. al. Use of a multiplex molecular beacon platform for rapid detection of methicillin and vancomycin resistance in *Staphylococcus aureus*. Journal of Clinical Microbiology, September 2005, p 4585-4591.

K. Mckernan, E. Gustafson, et. al. Methods of isolating nucleic acids using multifunctional group coated solid phase carriers. United States Patent Application Publication US 2006/0177836 A1, Aug. 10, 2006.

J. Farley, P. Stamper, et. al. Comparison of the BD GeneOhm methicillin-resistant *Staphylococcus aureus* (MRSA) PCR assay to culture by use of BBL CHROMagar MRSA for detection of MRSA in nasal surveillance cultures from an at-risk community population. Journal of Clinical Microbiology, February 2008, p 743-746.

R. Heusser, M. Ender, et al., Mosaic Staphylococcal Cassette Chromosome mec Containing Two Recombinase Loci and a New mec Complex, B2. Antimicrob. Agents Chemother. January 2007, p 390-393.

T. Ito, Y. Katayama, et. Al., Structural comparison of three types of staphylococcal cassette chromosome mec integrated in the chromosome in methicillin-resistant *Staphylococcus aureus*. Antimicrob. Agent Chemother. 2001, 45: p 1323-1336.

C. Heid, J. Stevens, et al., Real time quantitative PCR. Genome Research, 1996 6(10):986-994.

K Mullis and F Faloona, Specific synthesis of DNA in vitro via a polymerase-catalyzed chain reaction. Methods Enzymol. 1987; 155:335-50.

T. Ito, X. Ma et al., Novel Type V Staphylococcal Cassette mec Driven by a Novel Cassette Chromosome Recombinase, ccrC. Antimicrob. Agent Chemother. 2004, 48: P 2637-2651.

M. Noto, B. Kreiswirth, et al., Gene Acquisition at the Insertion Site for SCCmec, the Genomic Island Conferring Methicillin Resistance in *Staphylococcus aureus*, J. Bacteriol. 2008, 190:1276-1283.

Throughout this application various publications are referenced. The disclosures of these publications in their entireties are hereby incorporated by reference into this application for all purposes. None is admitted to be prior art.

What is claimed is:

1. A method for determining the presence of a biological entity in a sample, the method comprising:

detecting amounts of at least three genetic elements in the sample; and determining the presence of the biological entity in the sample by executing a call algorithm on a digital computer, wherein the call algorithm uses as inputs measured values associated with the at least three genetic elements and combines them to form a vector, which is compared to a boundary function on a 2-dimensional Y-plot comprising an origin, and if the vector is within the boundary function, the biological entity is present and if the vector is not within the boundary function, the biological entity is not present, and wherein vectors associated with the biological entity are generally closer to the origin than vectors that are not associated with the biological entity.

2. The method of claim 1 wherein the at least three genetic elements comprise mecA, SCCmec, and a *Staphylococcus aureus*-specific target gene sequence, and wherein the call algorithm combines the detected amounts of mecA, SCCmec, and the *Staphylococcus aureus*-specific target gene sequence as a vector, $\vec{p}$, on the 2-dimensional Y-plot.

3. The method of claim 2 wherein the vector $\vec{p}$ is defined by the formula:

$$\vec{p} = mecA * e^{0i} + SA * e^{\frac{2}{3}\pi i} + SCCmec * e^{\frac{4}{3}\pi i}.$$

4. The method of claim 2 further comprising displaying the Y-plot on a display.

5. The method of claim 2, wherein SCCmec is at an orfX junction.

6. The method of claim 2, wherein detection of an SCCmec/orfX junction indicates the presence of SCCmec.

7. The method of claim 1 wherein the at least three genetic elements comprise mecA, SCCmec, and femA.

8. The method of claim 1 wherein the biological entity comprises MRSA.

9. The method of claim 1 wherein the boundary function is defined by a rectangle gating function, circular gating process, a neural network, or a Gaussian distribution function.

10. The method of claim 1 wherein the boundary function is created from a set of known samples, wherein the presence of MRSA is known for each sample in the set of known samples.

11. A system for determining the presence of a biological entity in a sample, the system comprising:

a measurement module capable of detecting values associated with at least three genetic elements in the sample;

a memory storing the detected values from the measurement module;

a computer readable medium containing computer readable code having instructions for executing a call algorithm, wherein the call algorithm uses as inputs the detected and measured values of the at least three genetic elements and combines them to form a vector, which is compared to a boundary function on a 2-dimensional Y-plot comprising an origin, and if the vector is within the boundary function, the biological entity is present and if the vector is not within the boundary function, the biological entity is not present; and a processor to execute the computer readable code on the computer readable medium in order to determine the presence of the biological entity in the sample, and wherein vectors associated with the biological entity are generally closer to the origin than vectors that are not associated with the biological entity.

12. The system of claim 11 wherein the values are amounts of the at least three genetic elements.

13. The system of claim 11, and wherein the at least three genetic elements comprise mecA, SCCmec, and a *Staphylococcus aureus*-specific target gene sequence, and wherein the call algorithm combines the detected amounts of mecA, SCCmec, and the *Staphylococcus aureus*-specific target gene sequence as a vector, $\vec{p}$, on the 2-dimensional Y-plot.

14. The system of claim 13 wherein the vector $\vec{p}$ is defined by the formula:

$$\vec{p} = mecA * e^{0i} + SA * e^{\frac{2}{3}\pi i} + SCCmec * e^{\frac{4}{3}\pi i}.$$

15. The system of claim 13 further comprising a display for displaying the 2-dimensional Y-plot.

16. The system of claim 13, wherein SCCmec is at an orfX junction.

17. The system of claim 13, wherein detection of an SCCmec/orfX junction indicates the presence of SCCmec.

18. The system of claim 11 wherein the measurement module comprises a real time PCR apparatus.

19. The system of claim 11 wherein the boundary function is defined by a rectangle gating function, circular gating process, a neural network, or a Gaussian distribution function.

20. A non-transitory computer readable medium comprising:

code, executable by a processor, for performing a call algorithm, wherein the call algorithm uses as inputs detected and measured values of the at least three genetic elements and combines them to form a vector, which is compared to a boundary function on a 2-dimensional Y-plot comprising an origin, and if the vector is within the boundary function, a biological entity is present and if the vector is not within the boundary function, the biological entity is not present, and wherein vectors associated with the biological entity are generally closer to the origin than vectors that are not associated with the biological entity.

21. The computer readable medium of claim 20 wherein the boundary function is defined by a rectangle gating function, circular gating process, a neural network, or a Gaussian distribution function.

22. The computer readable medium of claim 20, and wherein the at least three genetic elements comprise mecA, SCCmec, and a *Staphylococcus aureus*-specific target gene sequence, and wherein the call algorithm combines the detected amounts of mecA, SCCmec, and the *Staphylococcus aureus*-specific target gene sequence as a vector, $\vec{p}$, on the 2-dimensional Y-plot.

23. The computer readable medium of claim 22 wherein the vector $\vec{p}$ is defined by the formula:

$$\vec{p} = mecA * e^{0i} + SA * e^{\frac{2}{3}\pi i} + SCCmec * e^{\frac{4}{3}\pi i}.$$

24. The computer readable medium of claim 22 further comprising code for displaying the 2-dimensional Y-plot.

25. The computer readable medium of claim 22, wherein SCCmec is at an orfX junction.

26. The computer readable medium of claim 22, wherein detection of an SCCmec/orfX junction indicates the presence of SCCmec.

27. A method for creating a model that can be used to determine the presence of a biological entity in an unknown sample, the method comprising:

detecting the presence and values of at least three genetic elements in known samples;

executing a call algorithm on a digital computer for each sample in the known samples, wherein the call algorithm creates vectors and uses as inputs for each vector the detected values of the at least three genetic elements, wherein some vectors are associated with the biological entity and some vectors are not associated with the biological entity;

plotting the vectors on a 2-dimensional Y-plot comprising an origin; and creating a boundary function separating the vectors that are associated with the biological entities and the vectors that are not associated with the biological entity, and wherein vectors associated with the biological entity are generally closer to the origin than vectors that are not associated with the biological entity.

28. The method of claim 27 wherein the boundary function is defined using a rectangle gating function, circular gating process, a neural network, or a Gaussian distribution function.

29. The method of claim 27 further comprising displaying the 2-dimensional Y-plot.

30. The method of claim 27 wherein the at least three genetic elements comprise mecA, SCCmec, and a *Staphylococcus aureus*-specific target gene sequence, and wherein the call algorithm combines the detected amounts of mecA, SCCmec, and the *Staphylococcus aureus*-specific target gene sequence as a vector, $\vec{p}$, on the 2-dimensional Y-plot.

31. The method of claim 30 wherein the vector $\vec{p}$ is defined by the formula:

$$\vec{p} = mecA * e^{0i} + SA * e^{\frac{2}{3}\pi i} + SCCmec * e^{\frac{4}{3}\pi i}.$$

32. The method of claim 30, wherein SCCmec is at an orfX junction.

33. The method of claim 30, wherein detection of an SCCmec/orfX junction indicates the presence of SCCmec.

* * * * *

SEQUENCE LISTING

```
<160> NUMBER OF SEQ ID NOS: 27

<210> SEQ ID NO 1
<211> LENGTH: 29
<212> TYPE: DNA
<213> ORGANISM: Artificial Sequence
<220> FEATURE:
<223> OTHER INFORMATION: synthetic femA PCR forward primer femA-3

<400> SEQUENCE: 1
gaccgttata atttctatgg tgttagtgg                                           29

<210> SEQ ID NO 2
<211> LENGTH: 27
<212> TYPE: DNA
<213> ORGANISM: Artificial Sequence
<220> FEATURE:
<223> OTHER INFORMATION: synthetic femA PCR reverse primer femA-3

<400> SEQUENCE: 2
gtcaccaaca tattcaataa tttcagc                                             27

<210> SEQ ID NO 3
<211> LENGTH: 26
<212> TYPE: DNA
<213> ORGANISM: Artificial Sequence
<220> FEATURE:
<223> OTHER INFORMATION: synthetic femA TaqMan probe femA-sa-probe

<400> SEQUENCE: 3
acagaagatg ctgaagatgc tggtgt                                              26

<210> SEQ ID NO 4
<211> LENGTH: 27
<212> TYPE: DNA
<213> ORGANISM: Artificial Sequence
<220> FEATURE:
<223> OTHER INFORMATION: synthetic mecA PCR forward primer mecA-2

<400> SEQUENCE: 4
gcagaaagac caaagcatac atattga                                             27

<210> SEQ ID NO 5
<211> LENGTH: 24
<212> TYPE: DNA
```

```
<213> ORGANISM: Artificial Sequence
<220> FEATURE:
<223> OTHER INFORMATION: synthetic mecA PCR reverse primer MecA-2

<400> SEQUENCE: 5
gcctatctca tatgctgttc ctgt                                            24

<210> SEQ ID NO 6
<211> LENGTH: 26
<212> TYPE: DNA
<213> ORGANISM: Artificial Sequence
<220> FEATURE:
<223> OTHER INFORMATION: synthetic mecA TaqMan probe mecAprobe

<400> SEQUENCE: 6
agaccgaaac aatgtggaat tggcca                                          26

<210> SEQ ID NO 7
<211> LENGTH: 24
<212> TYPE: DNA
<213> ORGANISM: Artificial Sequence
<220> FEATURE:
<223> OTHER INFORMATION: synthetic S. felis (IC) PCR forward primer
      Sfforwardnew

<400> SEQUENCE: 7
tgccaatgta gatagtcttc caga                                            24

<210> SEQ ID NO 8
<211> LENGTH: 22
<212> TYPE: DNA
<213> ORGANISM: Artificial Sequence
<220> FEATURE:
<223> OTHER INFORMATION: synthetic S. felis (IC) PCR reverse primer
      sfreversenew

<400> SEQUENCE: 8
aagtgcccag aagaatgagt gg                                              22

<210> SEQ ID NO 9
<211> LENGTH: 26
<212> TYPE: DNA
<213> ORGANISM: Artificial Sequence
<220> FEATURE:
<223> OTHER INFORMATION: synthetic S. felis (IC) probe fSfelis

<400> SEQUENCE: 9
accgccacca ttattacgta cagctg                                          26

<210> SEQ ID NO 10
<211> LENGTH: 26
<212> TYPE: DNA
<213> ORGANISM: Artificial Sequence
<220> FEATURE:
<223> OTHER INFORMATION: synthetic SCCmec PCR forward primer
      OrfX-ISS/attBScc for-1

<400> SEQUENCE: 10
tgagggttgt gttaattgag caagtg                                          26

<210> SEQ ID NO 11
<211> LENGTH: 26
<212> TYPE: DNA
<213> ORGANISM: Artificial Sequence
<220> FEATURE:
<223> OTHER INFORMATION: synthetic SCCmec PCR forward primer
      OrfX-ISS/attBScc for-2
```

<400> SEQUENCE: 11
tgcgggttgt gttaattgaa caagtg					26

<210> SEQ ID NO 12
<211> LENGTH: 28
<212> TYPE: DNA
<213> ORGANISM: Artificial Sequence
<220> FEATURE:
<223> OTHER INFORMATION: synthetic SCCmec PCR reverse primer
      mecII512-1-sccmec-3

<400> SEQUENCE: 12
tcacttttta ttcttcaaag atttgagc					28

<210> SEQ ID NO 13
<211> LENGTH: 33
<212> TYPE: DNA
<213> ORGANISM: Artificial Sequence
<220> FEATURE:
<223> OTHER INFORMATION: synthetic SCCmec PCR reverse primer
      primer11-1-sccmec-7

<400> SEQUENCE: 13
aaattgctac taaagaggat atggaaaacc atc				33

<210> SEQ ID NO 14
<211> LENGTH: 29
<212> TYPE: DNA
<213> ORGANISM: Artificial Sequence
<220> FEATURE:
<223> OTHER INFORMATION: synthetic SCCmec PCR reverse primer
      primer12-sccmec-8

<400> SEQUENCE: 14
ctctgcttta tattataaaa ttacggctg					29

<210> SEQ ID NO 15
<211> LENGTH: 33
<212> TYPE: DNA
<213> ORGANISM: Artificial Sequence
<220> FEATURE:
<223> OTHER INFORMATION: synthetic SCCmec PCR reverse primer
      newtypeiii-1-sccmec-14

<400> SEQUENCE: 15
cgtatgatat tgcaaggtat aatccaatat ttc				33

<210> SEQ ID NO 16
<211> LENGTH: 28
<212> TYPE: DNA
<213> ORGANISM: Artificial Sequence
<220> FEATURE:
<223> OTHER INFORMATION: synthetic SCCmec PCR reverse primer
      typeIVc-sccemc-2

<400> SEQUENCE: 16
cttgaaatga aagactgcgg aggctaac					28

<210> SEQ ID NO 17
<211> LENGTH: 30
<212> TYPE: DNA
<213> ORGANISM: Artificial Sequence
<220> FEATURE:
<223> OTHER INFORMATION: synthetic SCCmec PCR reverse primer NEWPRIMERS

<400> SEQUENCE: 17
tgagcttttt ccactcccat ttcttccaaa                                      30

<210> SEQ ID NO 18
<211> LENGTH: 32
<212> TYPE: DNA
<213> ORGANISM: Artificial Sequence
<220> FEATURE:
<223> OTHER INFORMATION: synthetic SCCmec PCR reverse primer SCCmec-4nV

<400> SEQUENCE: 18
gcaattcaca taaacctcat atgttctgat ac                                   32

<210> SEQ ID NO 19
<211> LENGTH: 32
<212> TYPE: DNA
<213> ORGANISM: Artificial Sequence
<220> FEATURE:
<223> OTHER INFORMATION: synthetic SCCmec PCR reverse primer SCCmec-3n

<400> SEQUENCE: 19
cattcattca tccaccctaa acttaatctt tc                                   32

<210> SEQ ID NO 20
<211> LENGTH: 34
<212> TYPE: DNA
<213> ORGANISM: Artificial Sequence
<220> FEATURE:
<223> OTHER INFORMATION: synthetic SCCmec PCR reverse primer SCCmec-5n

<400> SEQUENCE: 20
tatggaaatc catctctact ttattgtttt cttc                                 34

<210> SEQ ID NO 21
<211> LENGTH: 32
<212> TYPE: DNA
<213> ORGANISM: Artificial Sequence
<220> FEATURE:
<223> OTHER INFORMATION: synthetic SCCmec PCR reverse primer SCCmec-6n

<400> SEQUENCE: 21
aatatttcat atatgtaatt cctccacatc tc                                   32

<210> SEQ ID NO 22
<211> LENGTH: 32
<212> TYPE: DNA
<213> ORGANISM: Artificial Sequence
<220> FEATURE:
<223> OTHER INFORMATION: synthetic SCCmec PCR reverse primer SE-7-11

<400> SEQUENCE: 22
ctatttctgt aatacttaaa acctttctt cc                                    32

<210> SEQ ID NO 23
<211> LENGTH: 35
<212> TYPE: DNA
<213> ORGANISM: Artificial Sequence
<220> FEATURE:
<223> OTHER INFORMATION: synthetic SCCmec PCR reverse primer SE-17

<400> SEQUENCE: 23
ccgtatgatt catattaaaa tgaatcatac ggagg                                35

<210> SEQ ID NO 24
<211> LENGTH: 31
<212> TYPE: DNA

```
<213> ORGANISM: Artificial Sequence
<220> FEATURE:
<223> OTHER INFORMATION: synthetic SCCmec PCR reverse primer SE-13

<400> SEQUENCE: 24
cttcttatga aatgtctttt ttcacttatc c                                31

<210> SEQ ID NO 25
<211> LENGTH: 30
<212> TYPE: DNA
<213> ORGANISM: Artificial Sequence
<220> FEATURE:
<223> OTHER INFORMATION: synthetic SCCmec TaqMan probe orfx probe-2

<400> SEQUENCE: 25
atgcttctcc tcgcataatc ttaaaygctc                                  30

<210> SEQ ID NO 26
<211> LENGTH: 30
<212> TYPE: DNA
<213> ORGANISM: Artificial Sequence
<220> FEATURE:
<223> OTHER INFORMATION: synthetic SCCmec TaqMan probe ORFX PROBE-1

<400> SEQUENCE: 26
acgcttctcc acgcataatc ttaaatgctc                                  30

<210> SEQ ID NO 27
<211> LENGTH: 30
<212> TYPE: DNA
<213> ORGANISM: Artificial Sequence
<220> FEATURE:
<223> OTHER INFORMATION: synthetic SCCmec TaqMan probe ORFX PROBE

<400> SEQUENCE: 27
acgcctctcc tcgcataatc ttaaatgctc                                  30
```